United States Patent [19]

Goudie

[11] 4,444,981
[45] Apr. 24, 1984

[54] 10 OXO-4,5-DIHYDRO-10H-BENZO 5,6 CYCLOHEPH[1,2-B]PYRRYLS

[75] Inventor: Alexander C. Goudie, Harlow, England

[73] Assignee: Beecham Group Limited, England

[21] Appl. No.: 172,473

[22] Filed: Jul. 25, 1980

[30] Foreign Application Priority Data

Jul. 28, 1979 [GB] United Kingdom ............... 7926402

[51] Int. Cl.³ .................... C07D 209/70; A61K 31/40
[52] U.S. Cl. ..................................... 548/427; 424/274
[58] Field of Search ..................... 260/326.32, 326.27, 260/326.5 B; 548/427

[56] References Cited

U.S. PATENT DOCUMENTS 4,359,423 11/1982 Goudie et al. ...................... 548/427

Primary Examiner—Paul M. Coughlan, Jr.
Assistant Examiner—D. B. Springer
Attorney, Agent, or Firm—Jacobs & Jacobs

[57] ABSTRACT

A compound of formula (II):

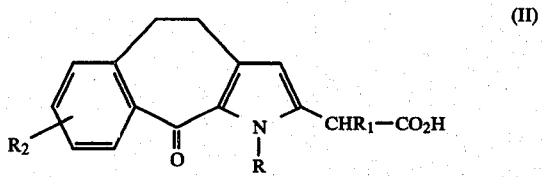

wherein
R is a $C_{1-4}$ alkyl group;
$R_1$ is a hydrogen atom or a $C_{1-4}$ alkyl group;
$R_2$ is a hydrogen or halogen atom, or a $C_{1-4}$ alkyl, $C_{1-4}$ alkoxy or $C_{1-4}$ alkylthio group;
and pro-drugs thereof; and the pharmaceutically acceptable salts of the compounds of formula (II) and of their pro-drugs; has useful anti-inflammatory and analgesic activity.

12 Claims, No Drawings

10 OXO-4,5-DIHYDRO-10H-BENZO 5,6 CYCLOHEPH[1,2-B]PYRRYLS

This invention relates to novel compounds having anti-inflammatory and analgesic activity, to a process for their preparation, and to pharmaceutical compositions containing them.

Tolmetin, a clinically used anti-inflammatory and analgesic agent of the formula (I):

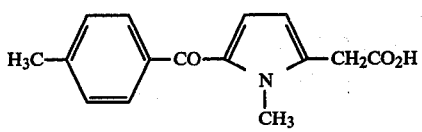

and related compounds have been described in J Pharmacol Exp Therap 1973, 185, 127-138, U.S. Pat. No. 3,752,826 and U.K. Patent Specification No. 1 195 628.

It has now been found that certain other structurally distinct acetic acid derivatives possess good anti-inflammatory and analgesic activity without undue gastric side effects.

Accordingly, the present invention provides the compounds of the formula (II):

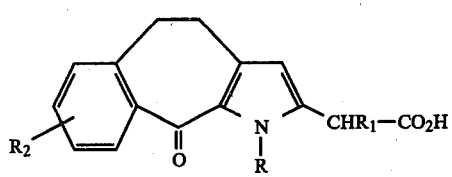

wherein
R is a $C_{1-4}$ alkyl group;
$R_1$ is a hydrogen atom or a $C_{1-4}$ alkyl group;
$R_2$ is a hydrogen or halogen atom, or a $C_{1-4}$ alkyl, $C_{1-4}$ alkoxy or $C_{1-4}$ alkylthio group;
and pro-drugs thereof; and the pharmaceutically acceptable salts of the compounds of formula (II) and of their pro-drugs.

Suitable examples of R include methyl and ethyl. Preferably R is methyl.

Suitable examples of $R_1$ include hydrogen, methyl and ethyl. More suitable $R_1$ is hydrogen. $R_1$ may also with advantage be methyl.

Suitable examples of $R_2$ include hydrogen; fluorine, chlorine, bromine; methyl, ethyl, propyl; methoxy; and methylthio. The position of substitution for $R_2$ is suitably the 6, 7 or 8 position, more suitably the 7 or 8 position. A preferred position of substitution for $R_2$, if present, is the 7 position. Most suitably $R_2$ is methyl or chlorine. Preferably $R_2$ is hydrogen.

From the aforesaid it will be appreciated that within formula (II) there is a sub-group of formula (III):

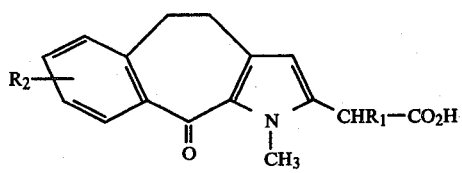

wherein $R_1$ is a hydrogen atom or methyl group and $R_2$ is a hydrogen, fluorine, chlorine or bromine atom or a methyl, ethyl, propyl, methoxy or methylthio group; and pharmaceutically acceptable salts and pro-drugs thereof.

Within this sub-group of formula (III) there is a preferred sub-group of formula (IV):

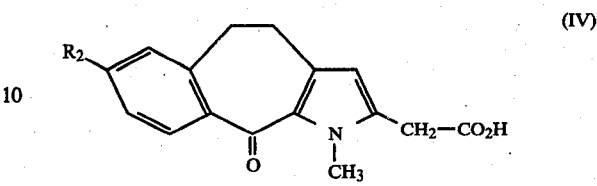

wherein $R_2$ is defined as in formula (III), and pharmaceutically acceptable salts and pro-drugs thereof.

Within formulae (III) and (IV) suitable and preferred examples of the variables are as described hereinbefore in regard to formula (II).

Particularly suitable pharmaceutically acceptable salts for this invention include alkali metal and alkaline earth metal salts such as the sodium, potassium, calcium and magnesium salts and salts of pharmaceutically acceptable nitrogenous bases such as the ammonium salt.

When used herein the term "pro-drug" means a compound metabolised in vivo to a compound of the formula (II) or its salt. A pro-drug may be identified by administering the pro-drug to a mammal such as a rat, mouse, monkey or man and identifying the compound of the formula (II) or its salt, for example in blood or urine.

When used herein the term "lower" means containing 1, 2, 3 or 4 carbon atoms. A particularly suitable lower alkyl group is the methyl group.

One class of pro-drugs of the compounds of the formula (II) are in vivo hydrolysable esters. Such esters may be simply substituted alkyl esters such as the methoxymethyl, 2-methoxyethyl, 2-hydroxyethyl, 2-dimethylaminoethyl, or benzyl esters of other esters conventionally used in the medical arts as pro-drugs such as a lower acyloxymethyl, α-lower acyloxyethyl, lower alkoxycarbonyloxymethyl, α-lower alkoxycarbonyloxymethyl, phthalidyl or like ester.

A further class of pro-drugs for the compounds of the formula (II) are in vivo hydrolysable amides thereof such as the primary amide, lower alkylamides and di- lower alkylamides thereof.

Another class of pro-drugs for the compounds of the formula (II) are the analogous compounds of lower oxidation state, namely the corresponding compounds in which the $CO_2H$ group is replaced by a CHO or $CH_2OH$ group.

A particularly suitable class of pro-drugs are those wherein the $CO_2H$ group of the compound of the formula (II)[or (III) and (VI)] is replaced by a group of the sub-formulae (a)–(j):

| | |
|---|---|
| $-CH_2-CO-CH_3$ | (a) |
| $-CH_2-CHOH-CH_3$ | (b) |
| $-CHOH-CHOH-CH_3$ | (c) |
| $-CHOH-CO-CH_3$ | (d) |
| $-CH_2-CH(OCOR_3)-CH_3$ | (e) |
| $-CH=C(OR_4)-CH_3$ | (f) |

$$-CH_2-C(OR_4)=CH_2 \qquad (g)$$

$$-CH_2-C(OR_5)OR_6-CH_3 \qquad (h)$$

$$-CH_2-C(OCOR_7)=CH_2 \qquad (i)$$

$$-CH=C(OCOR_7)-CH_3 \qquad (j)$$

In these sub-formulae $R_3$ is a phenyl or substituted phenyl group or a $C_{1-4}$ alkyl group optionally substituted by a phenyl or amino group (for example methyl and aminomethyl); $R_4$ is a lower alkyl group; $R_5$ and $R_6$ are each lower alkyl groups or are joined to represent a $CH_2CH_2$ or $CH_2CH_2CH_2$ group; and $R_7$ is a lower alkyl group.

Preferred pro-drugs are those containing sub-formulae (a), (b), (c), (d) and (e) as defined above. Particularly preferred pro-drugs are those containing sub-formulae (a) and (e).

Certain preferred compounds of this invention are 4,5-dihydro-1,7-dimethyl-10H-10-oxo-benzo[5,6]cyclohepta [1,2-b]pyrrole-2-acetic acid and its pharmaceutically acceptable salts and pro-drugs.

Other preferred compounds of this invention are 4,5-dihydro-7-chloro-10H-1-methyl-10-oxo-benzo[5,6-]cyclohepta[1,2-b]pyrrole-2-acetic acid and its pharmaceutically acceptable salts and pro-drugs.

Further preferred compounds of this invention are 4,5-dihydro-1OH-1-methyl-10-oxo-benzo[5,6]cyclohepta[1,2-b]pyrrole-2-acetic acid and its pharmaceutically acceptable salts and pro-drugs.

Certain preferred pro-drugs of this invention include 4-(4,5-dihydro-1,7-dimethyl-10H-10-oxo-benzo[5,6]cyclohepta[1,2-b]-2-pyrryl)butan-2-one; 4-(4,5-dihydro-7-chloro-10H-1-methyl-10-oxo-benzo[5,6]cyclohepta[1,2-b]-2-pyrryl)butan-2-one; and 4-(4,5-dihydro-10H-1-methyl-10-oxo-benzo[5,6]cyclohepta[1,2-b]-2-pyrryl)-butan-2-one.

The compounds of this invention are most suitably provided in crystalline form.

In a further aspect this invention provides a pharmaceutical composition which comprises a compound of the formula (II) and a pharmaceutically acceptable carrier.

The compositions of this invention are useful in treating rheumatic and arthritic conditions because of their anti-inflammatory and analgesic properties. The compositions may be adapted for administration via the oral, rectal or injection routes but since the compositions of this invention do not excessively irritate the gastrointestinal tract it is preferred that they are adapted for oral administration.

The compositions of this invention may contain diluents, binders, fillers, disintegrants, flavouring agents, colouring agents, lubricants, preservatives or the like in conventional manner. These conventional excipients may be employed in conventional manner, for example as in the preparation of compositions of ketoprofen, indomethacin, naproxen, acetylsalicyclic acid or other anti-inflammatory analgesic agents.

Most suitably the composition of this invention will be in the form of a unit dose such as a tablet, capsule or reconstitutable powder in a sachet. Such unit doses will generally contain from 20 mg to 1,000 mg and more suitably will contain from about 30 mg to 500 mg, for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 200 to 3,000 mg and more usually in the range of 300 to 3,000 mg for example 500 to 2,000 mg. Alternatively the unit dose may contain from 2 to 20 mg of active agent and may be administered in multiples if desired to give the preceeding daily dose.

A favoured form of the composition of this invention is a hard gelatin capsule containing the active agent. The active agent may be in the form of a powder, granulate or the like and may advantageously be in intimate mixture with a lubricant such as magnesium stearate.

A further favoured form of the composition of this invention is a tablet containing the active agent. The active agent may be in the form of a recompressed granulate of the active ingredient in intimate mixture with a lubricant such as magnesium stearate, a filler such as microcrystalline cellulose and disintegrant such as sodium starch glycollate.

This present invention also provides a method of treating inflammatory and/or painful conditions in mammals which comprises administering per day an effective amount, such as from 50 to 4,000 mg, of a compound of this invention and more usually from 100 to 3,000 mg for example from 100 to 1,500 of a compound of this invention.

Mammals which may be thus treated include humans and domestic animals such as dogs, cats or horses.

Most suitably the medicament will be administered orally as 2, 3 or 4 doses per day at the dose level previously indicated.

The invention also provides a process for the preparation of a compound of the formula (II), its pharmaceutically acceptable salts and pro-drugs.

For easy reference, the following Scheme shows a synthetic pathway leading to the compounds of the formula (II):

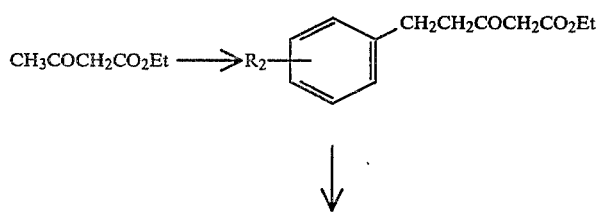

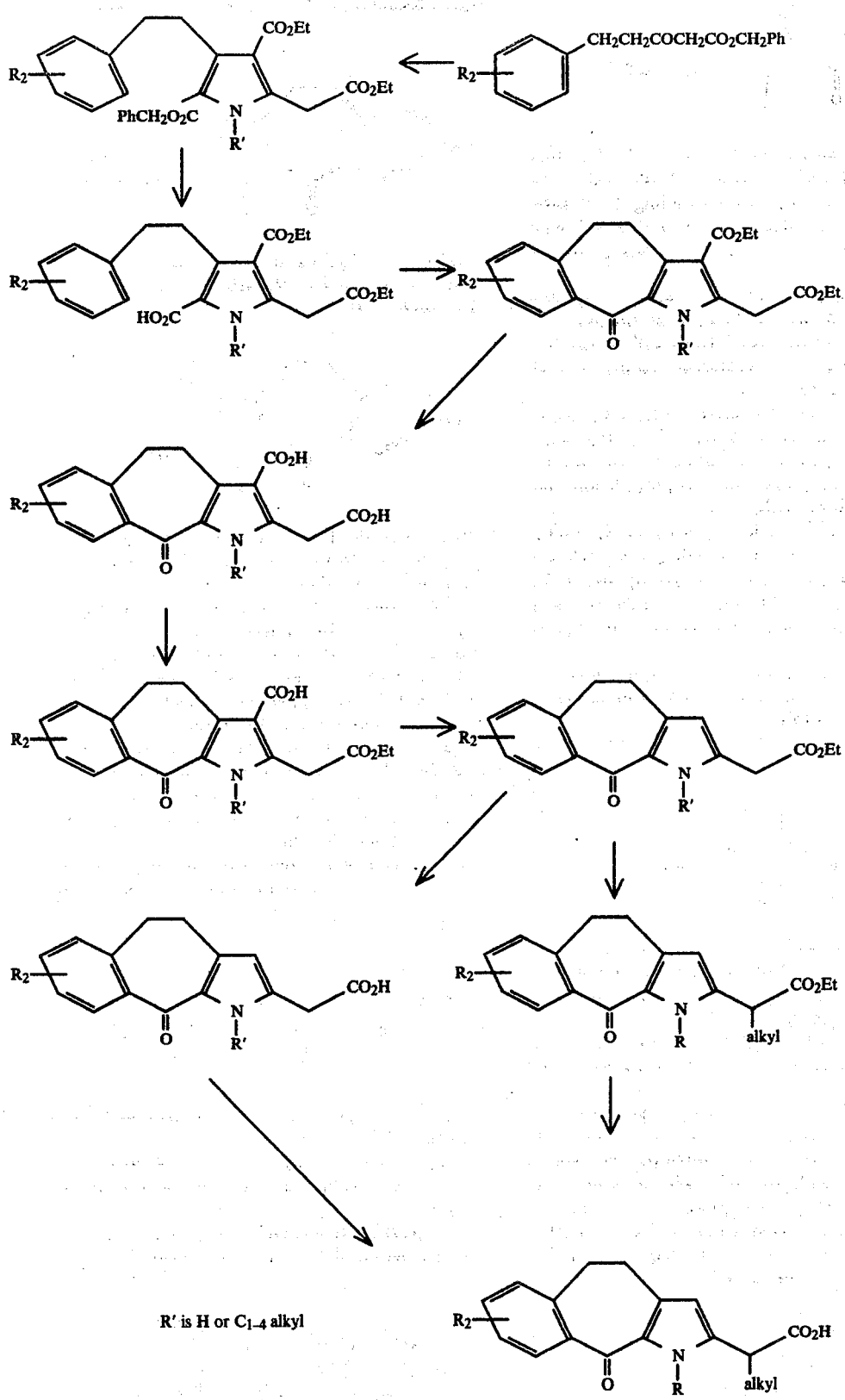
R' is H or C$_{1-4}$ alkyl
From the foregoing reaction Scheme it can be seen that the present invention provides a preferred process for the preparation of a compound of the formula (II) which comprises the basic hydrolysis of an ester of the formula (V):

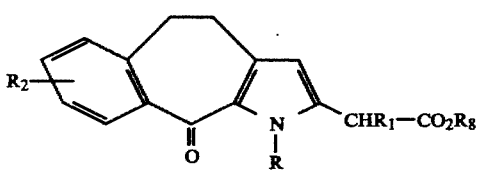

(V)

wherein $R_8$ is $C_{1-4}$ alkyl, such as ethyl, and the other variables are as defined in relation of formula (II); and thereafter if desired acidifying the resulting salt to form the free acid; and alkylating a compound in which $R_1$ is hydrogen to give the corresponding compound in which $R_1$ is alkyl.

The hydrolysis may be effected by using an hydroxide such as sodium hydroxide in aqueous ethanol.

The conversion of the thus formed salt to the free acid may be effected in conventional manner with an acid, such as hydrochloric acid.

The optional alkylation to convert a $R_1$ is hydrogen compound of formula (II) to a $R_1$ is $C_{1-4}$ alkyl compound of formula (II) can be carried out in conventional manner, for example with lithium diisopropylamide and an alkyl halide such as methyl iodide.

The compounds of formula (V) wherein $R_1$ is alkyl may be prepared from the corresponding compounds of the formula (V) wherein $R_1$ is hydrogen by alkylation. This alkylation may conveniently be carried out using sodium hydride and an alkyl halide such as methyl iodide.

Alternatively, in a further process of the invention for the preparation of compounds of the formula (II), a compound of formula (VI):

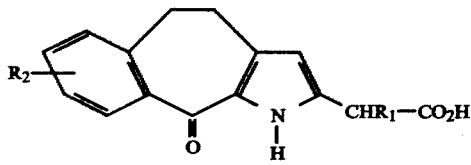

(VI)

is alkylated; and thereafter if desired a salt thereof is formed; or a compound of the formula (II) in which $R_1$ is hydrogen is alkylated to give the corresponding compound wherein $R_1$ is alkyl.

The alkylation of the compound of formula (VI) is suitably carried out using lithium diisopropylamide and dimethylsulphate.

If this alkylation reaction is on a compound of formula (VI) wherein $R_1$ is hydrogen, and is carefully controlled then a compound of formula (II) wherein $R_1$ is hydrogen will result. In such cases if desired the further conversion of the $R_1$ group to alkyl may be carried out by further reaction under similar conditions.

The compound of formula (VI) may be prepared from a compound of formula (V)':

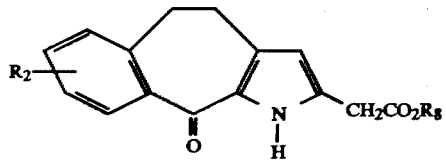

(V)' by basic hydrolysis as described in relation to formula (V).

The intermediates of formula (V)', and the intermediates of formula (V), may be written with structure (V)''

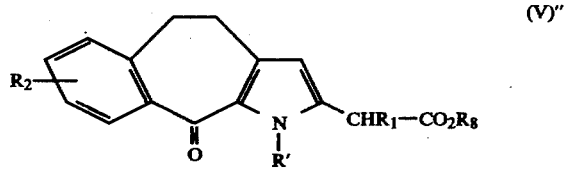

(V)'' wherein R' is hydrogen or $C_{1-4}$ alkyl; and may themselves be prepared by decarboxylation of a compound of formula (VII):

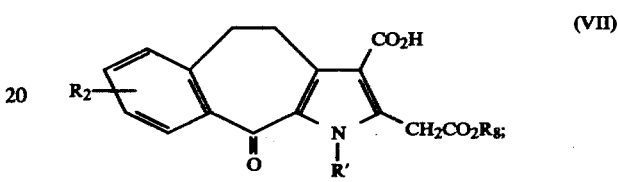

(VII)

and subsequent optional alkylation of a $R_1$ is hydrogen compound of formula (V)'' to give a compound of the formula (V)'' wherein $R_1$ is alkyl.

This decarboxylation may best be achieved by heating in an inert atmosphere, at a temperature such as 170°–240° C. Alternatively a high boiling point solvent such as diethyl formamide, ethanolamine or quinoline (with or without copper) may be used in the reaction. When R' is alkyl in the thus formed compound of formula (V)'', then the optional $R_1$ alkylation can be carried out using sodium hydride and an alkyl halide. When R' is hydrogen in the thus formed compound, then the optional $R_1$ alkylation can be carried out using $K_2CO_3$ and an alkyl halide.

Compounds of formula (VII) may be prepared by the de-esterification of a compound of formula (VIII):

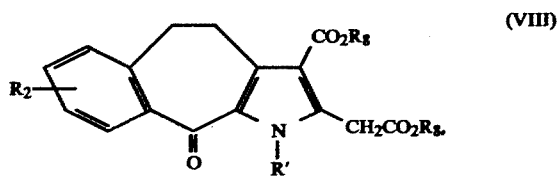

(VIII)

and then subsequent selective esterification of the acetic acid function.

These reactions may be carried out in conventional manner, for example as illustrated in the specific Descriptions.

Compounds of formula (VIII) may be prepared by the cyclisation of a compound of formula (IX):

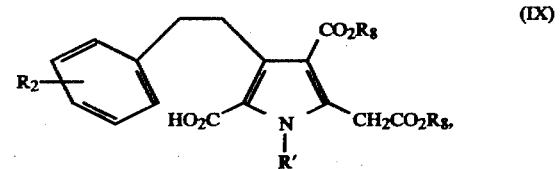

(IX)

followed by optional alkylation of a thus formed compound of formula (VIII) wherein R' is hydrogen (with for example $K_2CO_3$ and dimethylsulphate).

This cyclisation reaction is suitably carried out with a strong acid, such as polyphosphoric acid or methane sulphonic acid/$P_2O_5$. When R' is alkyl, the cyclisation may also be carried out by a Friedel-Crafts reaction, using a Lewis acid such as $AlCl_3$ or $SnCl_4$ and the acid of formula (IX) in the form of its acid chloride or mixed anhydride.

Compounds of the formula (IX) may themselves be prepared by reacting a compound of formula (X):

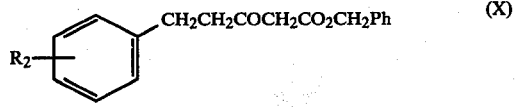

in a Knorr synthesis; and subsequently, if necessary, alkylating the pyrrole N-hydrogen; and then converting the benzyl ester to the free acid.

The Knorr pyrrole synthesis is suitably carried out with sodium nitrite, diethyl acetone-1,3-dicarboxylate and zinc, in acetic acid.

The N—H alkylation may suitably be carried out with $K_2CO_3$ and a dialkyl sulphate such as dimethyl sulphate.

The description above describes suitable processes for preparing the compounds of formula (II). There are however a number of process variations which should be noted.

(i) Instead of the compound of formula (X), the corresponding dialkylamide or morpholide may be used, in which case suitably $POCl_3$ may be used in the subsequent cyclisation reaction, with or without a solvent.

(ii) Any readily hydrolysable or hydrogenolysable ester may be used in the place of the benzyl ester in the compound of formula (X). For example the t-butyl ester may be used, and after the Knorr pyrrole synthesis hydrolysis thereof is simply achieved with dilute hydrochloric acid.

(iii) $R_2$ groups may be interchanged at suitable points in the synthetic sequence. For example when $R_2$ is 7-fluoro compounds of the formula (VIII) may be converted to the corresponding $R_2$ is alkoxy or alkyl thio compounds by reaction with a source of alkoxide or alkylthio ion.

(iv) The cyclisation reaction may be carried out exactly as described above, but on a compound of the formula (IX)':

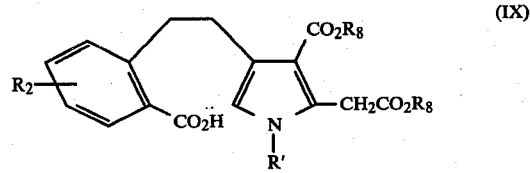

This compound of formula (IX)' may be derived from the corresponding compound of formula (IX) by thermal decarboxylation. Otherwise the compound of formula (IX)' may be prepared in analogous manner to the compounds of formula (IX) but using a readily hydrolysable or hydrogenolysable (eg benzyl) ester of a compound of formula (X)':

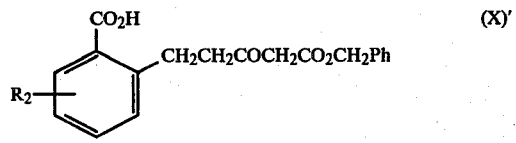

It will be appreciated that in this alternative cyclisation scheme variations (i) and (ii) above may be incorporated if desired.

The salts of the compounds of formula (II) may be prepared from the free acids of the formula (II) in any of the conventional ways used to convert an acid to its salt.

The pro-drugs of the compounds of the formula (II) may either be prepared from the compounds of formula (II), or may be synthesised "independently", as appropriate.

All such processes of course form part of this invention.

Examples of preparation of pro-drugs from compounds of the formula (II) include esterification and amidation.

Examples of "independent" synthesis include the preparation of a compound of the formula (II) wherein the $CO_2H$ group is replaced by a $CH_2COCH_3$ group (ie sub-formula (a)), by the oxidation of a compound of the formula (XI):

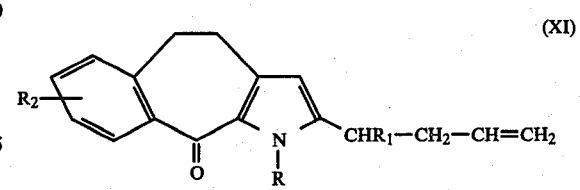

This oxidation may be carried out in any convenient manner for example with oxygen in aqueous dimethylformamide in the presence of palladium chloride and cuprous chloride. This oxidation reaction may be effected using pure oxygen or air. In general it is sufficient to blow air through the reaction mixture at an ambient or slightly elevated temperature to effect oxidation. The desired compound may be obtained from the reaction mixture by dilution with water followed by extraction into water-immiscible solvent such as chloroform which may then be dried and evaporated. This initial crude material may be purified chromatographically if desired, for example by column chromatography over silica gel using 1:1 ether: petrol eluant.

The compounds of the formula (XI) may be prepared by the decarboxylation of a corresponding compound of the formula (XII):

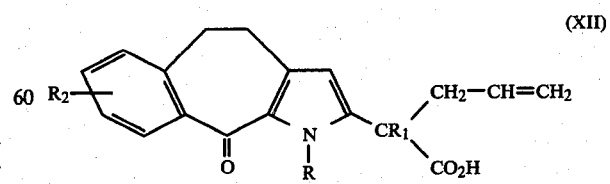

The decarboxylation may be effected by heating, for example to 170°–210° C. The desired product may be obtained by trituration using a non-hydroxylic solvent such as chloroform.

The acid of the formula (XII) may be obtained by hydrolysis of the corresponding $C_{1-4}$ alkyl ester such as the ethyl ester using normal sodium hydroxide solution followed by neutralisation with hydrochloric acid. This $C_{1-4}$ alkyl ester may be prepared by the allylation of the corresponding compound of the formula (V). Such allylations may be brought about by generating an anion of the formula (V) for example with sodium hydride in dimethoxyethane, and quenching said anion with allyl bromide.

Alternatively, compounds of the formula (XII) may be prepared by the direct allylation of a compound of formula (II) with for example allyl bromide in the presence of lithium diisopropylamide.

The pro-drugs of compounds of the formula (II) wherein the $CO_2H$ group is replaced by a $CH_2COCH_3$ group may also be prepared by thermal decomposition of a compound of formula (XIII):

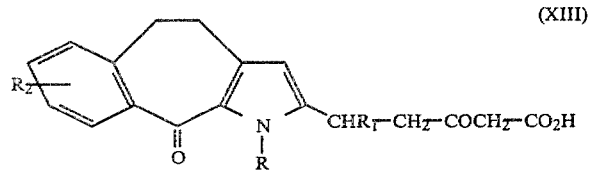

(XIII)

This decomposition may suitably be carried out with or without an inert solvent, such as dimethyl sulphoxide, at about 60° to 100° C.

The intermediate of formula (XIII) may themselves be prepared from a compound of formula (XIV):

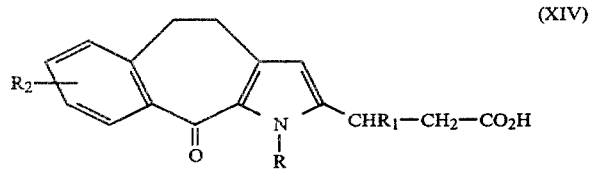

(XIV)

via a suitably activated derivative such as the ethoxycarbonyl derivative, for example following the general method described in Synthesis 1979, p. 787.

It will be appreciated that the compounds of formula (XIV) may be prepared in analogous manner to the preparation of the corresponding compounds of formula (II) except that dimethyl 3-oxoadipate is suitably used in the Knorr pyrrole synthesis reaction.

Compounds of the formula (II) wherein the $CO_2H$ group is replaced by a group of the sub-formula (b) may be prepared by the reduction of a corresponding compound of the formula (II) wherein the $CO_2H$ group is replaced by a group of the sub-formula (a). Such a reduction may use a complex hydride such as sodium borohydride. Mild conditions and avoidance of excess reagent prevent reduction of the aromatic carbonyl. The desired compound may be purified by conventional methods of column chromatography.

Pro-drugs of the compounds of the formula (II) containing a group of the sub-formulae (e), (f), (g), (h), (i) and (j) may be prepared, for example as described in Belgian Pat. No. 866 857 (or Offenlegungsschrift No. P 28 19 463.0).

Thus compounds of the formula (II) wherein the $CO_2H$ group is replaced by the sub-formula (e) may be prepared by the acylation of a corresponding compound containing the sub-formula (b). Suitable methods of acylation include those described in Belgian Pat. No. 854 429 (or Offenlegungsschrift No. P 28 19 463.0).

Compounds of the formula (II) wherein the $CO_2H$ group is replaced by sub-formula (f) or (j); (g) or (i); or (h); may be prepared by the enol acylation or enol etherification of a corresponding compound containing the sub-formula (a). Suitable methods of enol acylation or enol etherification include those described in Offenlegungsschrift No. P 26 47 966.3.

Also, compounds of the formula (II) wherein the $CO_2H$ group is replaced by a group of the sub-formula (d) may be prepared by the reaction of m-chloroperbenzoic acid and a compound of the formula (II) in which the $CO_2H$ group is replaced by a group of the sub-formula (f). Such reactions are generally carried out at 0°-5° C. in mixed solvents such as diethyl ether/water.

Compounds of the formula (II) wherein the $CO_2H$ group is replaced by a group of the sub-formula (c) may be prepared by reduction of a corresponding compound of the formula (II) in which the $CO_2H$ group is replaced by a group of the sub-formula (d). Such a reaction may be effected using sodium borohydride under conventional conditions.

As stated hereinbefore, other pro-drugs of the compound of formula (II) include the corresponding aldehyde and alcohol. The aldehyde may be prepared from the acid by reduction, for example via the acid halide (suitably chloride) in a Rosemund reduction. The alcohol may be prepared by reduction of the aldehyde, for example with sodium borohydride.

It will be appreciated that in the same way that, as hereinbefore described, the preparation of compounds of the formula (II) may entail as a last stage the alkylation of a N-hydrogen atom or the pyrrole moiety, the same can be true for the aforedescribed pro-drugs. Of course the N—H pro-drug intermediates for such a last stage alkylation can be prepared in analogous process to the corresponding N-alkyl pro-drugs.

The intermediates of formulae (V)″, (VI), (VII), (VIII), (XI), (XII), (XIII) and (XIV) form an important part of this invention.

The following Descriptions illustrate the preparation of intermediates. The following Examples illustrate the preparation of the compounds of this invention.

DESCRIPTION 1(a)

Ethyl 3-oxo-5-m-toluylpentanoate

Ethyl acetoacetate (16.0 g; 0.123 mole) was added dropwise with stirring under nitrogen to 50% sodium hydride (6.5 g; 0.135 mole) in dry tetrahydrofuran (300 ml) at 0°. The resulting solution was stirred for 10 minutes at 0° before adding a solution of n-butyl lithium in hexane (95 ml, 1.6 M; 0.152 mole) dropwise. The resulting yellowish orange dianion solution was stirred for 10 minutes at 0° before adding α-bromo-m-xylene (34 g, 0.189 mole) in ether (20 ml) and allowed to warm to room temperature 30 minutes after completing the addition. The reaction mixture was quenched by addition of conc. HCl (25 ml) in $H_2O$ (60 ml) followed by ether (180 ml). The layers were separated and the aqueous further extracted with ether (3 × 125 ml). The combined organic layers were washed with water until the wash was neutral, then dried (anhydrous $MgSO_4$) and evaporated to dryness. The resulting yellow oil was distilled under vacuum to give a pale yellow oil (22.0 g, 76%), b.p. 132°–139° at 0.19 mmHg, n.m.r. δ($CDCl_3$) 7.07 (4H, m), 4.25 (2H, q, J=7 Hz), 3.47 (2H, s), 2.95 (4H, s), 2.40 (3H, s) and 1.35 (3H, t, J=7 Hz).

DESCRIPTION 1(b)

Benzyl 3-oxo-5-m-toluylpentanoate

The above ethyl ester (22.5 g, 0.096 mole) was heated between 170° and 210° under nitrogen with benzyl alcohol (8.2 g, 0.076 mole) for 3½ hours, the ethanol formed being distilled from the reaction mixture. The resulting pale yellow oil was essentially pure product, slightly contaminated by starting materials, n.m.r. $\delta(CDCl_3)$ 7.35 (5H, s), 7.03 (4H, m), 5.14 (2H, s), 3.44 (2H, s), 2.82 (4H, s) and 2.29 (3H, s).

DESCRIPTION 1(c)

5-Benzyl diethyl 4-(2-m-toluyl)ethyl pyrrole-2-acetate-3, 5-dicarboxylate

Sodium nitrite (1.67 g) in water (2.5 ml) was added slowly between 5° and 7° with stirring to the above crude benzyl ester (6.75 g, 0.023 mole based on 80% purity) in glacial acetic acid (14 ml). After completing the addition the mixture was stirred for a further 30 minutes at 0° then for 4 hours at room temperature before adding to diethyl acetone-1, 3-dicarboxylate (4.75 g, 0.023 mole) in glacial acetic acid (20 ml) at 70°. Zinc powder (5.1 g, 90%, 0.07 mole) and anhydrous sodium acetate (5.76 g) were added concurrently to the above mixture such that the temperature was maintained as near as possible to 100°. After these additions the mixture was refluxed for 1 hour before pouring into water (500 ml). On leaving to stand overnight a sticky yellow crystalline solid had formed which was purified by column chromatography using silica gel (300 g) and ether as eluant followed by recrystallisation from 60°-80° petrol ether to give a white solid (3.77 g, 34%) m.p. 104°-106°, n.m.r. $\delta(CDCl_3)$ 10.4 (1H, br., s), 7.39 (5H, s), 6.98 (4H, m), 5.33 (2H, s), 4.30 (2H, q, J=7 Hz), 4.18 (2H, q, J=7 Hz), 3.7-2.4 (4H, broad symmetrical multiplet), 2.29 (3H, s), 1.34 (3H, t, J=7 Hz), and 1.23 (3H, t, J=7 Hz). (Found: C, 70.26; H, 6.24; N, 2.83, $C_{28}H_{31}NO_6$ requires: C, 70.42; H, 6.54; N, 2.93%).

DESCRIPTION 1(d)

Diethyl 4-(2-m-toluyl)ethyl pyrrole-2-acetate-3-carboxylate-5-carboxylic acid

The pyrrole triester (11.86 g, 0.025 mole) was hydrogenated at atmospheric pressure overnight with 10% Pd/C (0.5 g) in methanol (500 ml). The catalyst was filtered off and the filtrate evaporated to dryness to give a quantitative yield of the required product as a white solid, n.m.r. $\delta(CDCl_3)$ 10.5 (2H, br., s), 7.1 (4H, m), 4.32 (2H, q, J=7 Hz), 4.2 (2H, q, J=7 Hz), 4.07 (2H, s), 3.7-2.5 (4H, broad symmetrical multiplet), 2.3 (3H, s), 1.38 (3H, t, J=7 Hz) and 1.28 (3H, t, J=7 Hz).

DESCRIPTION 1(e)

Diethyl 4,5-dihydro-10H-7-methyl-10-oxobenzo[5,6]cyclohepta[1,2-b]pyrrole-2-acetate-3-carboxylate The acid from the previous stage (9.66 g, 0.025 mole) was dissolved in dichloromethane (1.4 L) and phosphoric anhydride (59 g) dissolved in methane sulphonic acid (415 g) was added with stirring. The reaction was quenched after 24 hours by pouring carefully into ice/water with stirring. The organic layer was separated, washed several times with water followed by saturated aqueous sodium bicarbonate and finally water. The organic layer was dried (anhydrous $MgSO_4$) and evaporated to dryness to give a brown solid (9.46 g). The crude product was washed with ether/60°-80° petrol ether to give a pink solid (3.9 g, 43%). The product was further purified by recrystallisation from ether/petrol or chloroform/hexane to give a white crystalline solid m.p. 170°-173°, n.m.r. $\delta(CDCl_3)$, 11.17 (1H, br., s), 7.93 (1H d, J=8 Hz), 7.12 (1H, d, J=8 Hz), 7.07 (1H, s), 4.28 (2H, q, J=7 Hz), 4.17 (2H q, J=7 Hz), 4.15 (2H, s), 3.6-2.8 (4H, m), 2.38 (3H, s), 1.36 (3H, t, J=7 Hz) and 1.24 (3H, t, J=7 Hz). Observed $M^+ = 369.1584$.

DESCRIPTION 1(f)

Diethyl 4,5-dihydro-1,7-dimethyl-10H-10-oxo-benzo[5,6]cyclohepta[1,2-b]pyrrole-2-acetate-3-carboxylate A sample of crude tricyclic pyrrole diester (800 mg, 0.0022 mole) was refluxed for 30 hours in iso-butyl methylketone (20 ml) with potassium carbonate (800 mg) and dimethyl sulphate (560 mg, 0.0043 mole) and then poured into water. After extraction with chloroform (3×15 ml), drying (anhydrous $MgSO_4$) and evaporation to dryness, an orange gum was recovered which was purified by column chromatography (silica gel eluted with 3:1 60°-80° petrol:ether rising to 1:1). Recrystallisation from 60°-80° petrol gave a white solid (234 mg, 28%) m.p. 105°-109°, n.m.r. $\delta(CDCl_3)$ 7.83 (1H, d, J=8 Hz), 7.14 (1H, d, J=8 Hz), 7.07 (1H, s), 4.32 (2H, q, J=7 Hz), 4.21 (2H, q, J=7 Hz), 4.19 (2H, s), 3.5-2.8 (4H, m), 2.38 (3H, s), 1.35 (3H, t, J=7 Hz), and 1.28 (3H, t, J=7 Hz).

DESCRIPTION 1(g)

4,5-Dihydro-1,7-dimethyl-10H-10-oxo-benzo[5,6]cyclohepta[1,2-b]pyrrole-2-acetic acid-3-carboxylic acid The above diethyl ester (234 mg, 0.61 mmole) was refluxed with 25% NaOH (3 ml) for 3 hours then left to stand overnight before pouring into water, extracting with ether (3×25 ml) and acidifying the aqueous layer with dilute HCl. The resulting white precipitate was collected by filtration and dried to give the product as an off-white solid (191 mg, 96%), n.m.r. $\delta(d_6\text{-}DMSO)$ 7.69 (1H, d, J=8 Hz), 7.15 (1H, d, J=8 Hz), 7.1 (1H, s), 4.19 (2H, s), 3.85 (3H, s), 3.4-2.5 (4H, m), and 2.31 (3H, s).

DESCRIPTION 1(h)

Ethyl 4,5-dihydro-1,7-dimethyl-10H-10-oxo-benzo[5,6]cyclohepta[1,2-b]pyrrole-2-acetate-3-carboxylic acid A suspension of the above acid (190 mg, 0.58 mmole) was refluxed with 0.65% ethanolic HCl (3.4 ml) for 45 minutes by which time a clear solution had formed. On leaving to cool to room temperature a white solid precipitated. This was collected by filtration, washed with a little cold ethanol and dried to give the required product (148 mg, 72%) n.m.r. $\delta(d_6\text{-}DMSO)$ 7.70 (1H, d, J=8 Hz), 7.17 (1H, d), 7.13 (1H, s), 4.25 (2H, s), 4.12 (2H, q, J=7 Hz), 3.86 (3H, s), 3.50-2.65 (4H, m), 2.32 (3H, s), and 1.18 (3H, t, J=7 Hz).

DESCRIPTION 1(j)

Ethyl 4,5-dihydro-1,7-dimethyl-10H-10-oxo-benzo[5,6]cyclohepta[1,2-b]pyrrole-2-acetate The above acid (145 mg, 0.41 mmole) was heated under nitrogen at 190°–215° in an oil bath for 2 hours. Evolution of a gas was observed. The crude product (79 mg, 62%) was purified by column chromatography using silica gel and elution with 1:1 ether: 60°–80° petrol, n.m.r. δ(CDCl₃) 7.9 (1H, d, J=8 Hz), 7.1 (1H, d, J=8 Hz), 6.99 (1H, s), 5.94 (1H, s), 4.19 (2H, q, J=7 Hz), 3.94 (3H, s), 3.63 (2H, s), 3.2–2.6 (4H, m), 2.34 (3H, s) and 1.26 (3H, 6, J=7 Hz).

EXAMPLE 1

4,5-Dihydro-1,7-dimethyl-10H-10-oxo-benzo[5,6]cyclohepta[1,2-b]pyrrole-2-acetic acid

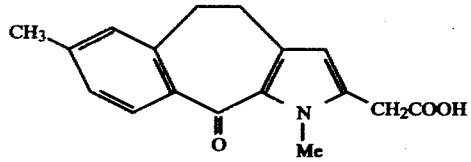

The above ester (79 mg, 0.25 mmole) was refluxed in 1 N NaOH (3 ml) with ethanol (0.5 ml) for 1 hour. The resulting clear yellow solution was cooled, diluted with water, extracted with ether (3×25 ml), and the aqueous layer filtered and acidified. The precipitate was collected by filtration and dried to give a white solid (63.5 mg, 88%), m.p. 142°–145° (m.p. 151°–152° after recrystallisation from CHCl₃/60°–80° petrol), n.m.r. δ(CDCl₃) 7.83 (1H, s), 7.85 (1H, d, J=8 Hz), 7.1 (1H, d), 6.99 (1H, s), 5.94 (1H, s), 3.91 (3H, s), 3.66 (2H, s), 3.2–2.6 (4H, m) and 2.33 (3H, s). Observed M⁺=283.1202.

DESCRIPTION 2(a)

Ethyl 3-oxo-5-phenylpentanoate

Ethyl acetoacetate (100 ml, 0.79 mole) in dry tetrahydrofuran (400 ml) was added dropwise with stirring under nitrogen to 50% sodium hydride (41.8 g, 0.87 mole) in dry tetrahydrofuran (80 ml) at 0° C. The resulting solution was stirred for 15 minutes at 0° C. before adding dropwise a solution of n-butyllithium in hexane (460 ml, 1.95 M; 0.90 mole). The resulting orange solution was stirred for a further 15 minutes at 0° C. before adding benzyl chloride (135 ml, 1.18 mole) in dry ether (200 ml) and the solution was then allowed to warm to room temperature over 1¼ hours with stirring before quenching reaction by addition of conc HCl acid (100 ml) in water (200 ml) followed by ether (500 ml). The layers were separated and the aqueous further extracted with ether (3×300 ml). The combined organic layers were washed with water until the wash was neutral, dried (anhydrous MgSO₄) and then concentrated. The resulting yellow oil was distilled under vacuum to give a virtually colourless oil (64.2 g, 37%), b.p. 118°–126° C. at 0.7 mmHg, n.m.r. δ(CDCl₃) 7.08 (5H, s), 4.07 (2H, q, J=7 Hz), 3.23 (2H, s), 2.80 (4H, s) and 1.23 (3H, t, J=7 Hz).

DESCRIPTION 2(b)

Benzyl 3-oxo-5-phenylpentanoate

Ethyl 3-oxo-5-phenylpentanoate (64.2 g, 0.29 mole) was heated between 190° and 210° C. under nitrogen with benzyl alcohol (28.9 ml, 0.28 mole) for 6 hours, the ethanol formed being distilled out of the reaction mixture. The resulting pale yellow oil was essentially pure product, slightly contaminated by starting materials, n.m.r. δ(CCl₄) 7.23 (5H, s), 7.06 (5H, s), 5.03 (2H, s), 3.23 (2H, s) and 2.73 (4H, s).

DESCRIPTION 2(c)

5-Benzyl diethyl 4-(2-phenylethyl)-pyrrole-2-acetate-3,5-dicarboxylate

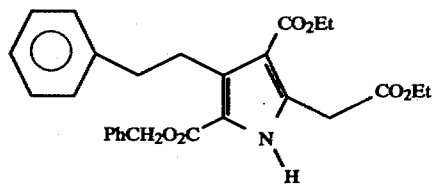

In a similar manner to Description 1(c), benzyl 3-oxo-5-phenylpentanoate (101.6 g, 0.36 mole) in glacial acetic acid (240 ml) was treated with a solution of sodium nitrite (33 g) in water (50 ml). Subsequent reaction with diethyl acetone-1,3-dicarboxylate (94.3 g) and zinc (102 g) afforded the required product (81.22 g, 49%) after work-up and recrystallization from toluene/60°–80° petroleum ether, m.p. 100°–103° C., δ(CDCl₃) 10.2 (1H, br, s), 7.3 (5H, s), 7.07 (5H, m), 5.25 (2H, s), 4.26 (2H, q, J=7 Hz), 4.15 (2H, q, J=7 Hz), 4.02 (2H, s), 3.5–2.4 (4H, symmetrical m), 1.33 (3H, t, J=7 Hz) and 1.24 (3H, t, J=7 Hz). (Found: C, 69.80; H, 6.29; N, 3.10. C₂₇H₂₉NO₆ requires: C, 69.96; H, 6.31; N, 3.02%).

DESCRIPTION 2(d)

5-Benzyl diethyl 1-methyl-4-(2-phenylethyl)pyrrole-2-acetate-3,5-dicarboxylate

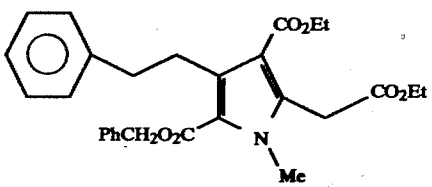

A stirred suspension of anhydrous potassium carbonate (81 g) with dimethyl sulphate (33 ml, 0.35 mole) and the N-H pyrrole from Description 2(c) (81 g, 0.175 mole) in isobutyl methyl ketone (800 ml) was refluxed overnight. A further amount of dimethyl sulphate (10 ml) and potassium carbonate (10 g) was added and the mixture refluxed for a further 5 hours before pouring into water (1,000 ml), separating the layers and washing the aqueous with ethyl acetate (3×200 ml). The combined organic layers were washed with water (2×200 ml), dried with anhydrous magnesium sulphate, filtered and the solvent evaporated. The product was purified by crystallization from toluene/60°–80° petrol to give a white solid (70.04 g, 84%), m.p. 84°–86°, δ(CDCl₃) 7.31 (5H, s), 7.06 (5H, m), 5.28 (2H, s), 4.25 (2H, q, J=7 Hz), 4.17 (2H, q, J=7 Hz), 4.08 (2H, s), 3.79 (3H, s), 3.6–2.4 (4H, symmetrical m). (Found: C, 70.49; H, 6.57; N, 3.01. $C_{28}H_{31}NO_6$ requires: C, 70.42; H, 6.54; N, 2.93%).

DESCRIPTION 2(e)

Diethyl 4-(2-phenylethyl)pyrrole-2-acetate-3-carboxylate-5-carboxylic acid

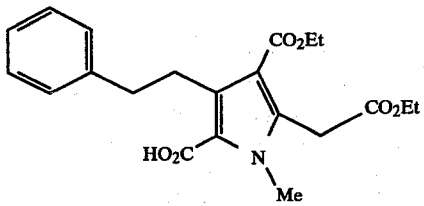

The benzyl ester from Description 2(d) (68.98 g, 0.145 mole) in ethyl acetate (1,000 ml) was hydrogenated at atmospheric pressure over 10% palladium on charcoal (3.5 g). When the theoretical amount of hydrogen had been taken up the catalyst was filtered off and the filtrate evaporated to dryness to give a white solid (53.2 g, 95%), δ(CDCl$_3$) 11.83 (1H, br., s), 7.2 (5H, br., s), 4.28 (2H, q, J=7 Hz), 4.13 (2H, q, J=7 Hz), 4.1 (2H, s), 3.83 (3H, s), 3.7–2.6 (4H, symmetrical m), 1.33 (3H, t, J=7 Hz), and 1.25 (3H, t, J=7 Hz).

DESCRIPTION 2(f)

Diethyl 4,5-dihydro-10H-1-methyl-10-oxobenzo-[5,6]cyclohepta[1,2-b]pyrrole-2-acetate-3-carboxylate

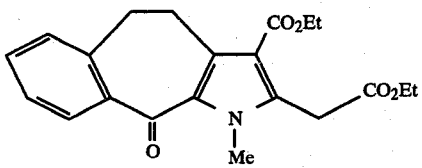

The acid from Description 2(e) (53 g, 0.137 mole) with oxalylchloride (26.1 g, 0.206 mole) in dry toluene (800 ml) was heated to reflux for 6 hours. After cooling and evaporating to dryness the resulting acid chloride was dissolved in dichloromethane (600 ml), powdered aluminium chloride (21.3 g, 0.16 mole) added in portions with stirring and then the mixture refluxed for 5½ hours. The reaction was followed by u.v. spectroscopy and by t.l.c. After leaving to stand overnight at room temperature the mixture was poured onto ice/water (500 ml), allowed to stir for 1 hour and the layers separated. The aqueous layer was extracted with dichloromethane (3×200 ml), the combined organics washed with water (2×200 ml), dried (anhydrous MgSO$_4$) and the solvent evaporated to give a red oil. N.m.r. spectroscopy of the crude product indicated that a conversion greater than 70% had been obtained. A small sample was purified by column chromatography on silica gel with 1:1 ether:60°-80° petroleum ether as eluant. The fractions containing the required product were recrystallized from 60°-80° petroleum ether to give a white crystalline solid, m.p. 71°-72°, δ(CDCl$_3$) 7.9–7.7 (1H, m), 7.0–7.5 (3H, m), 4.5–3.9 (4H, overlapping q, J=7 Hz), 4.14 (2H, s), 3.93 (3H, s), 3.5–2.8 (4H, m), 1.32 (3H, t, J=7 Hz) and 1.22 (3H, t, J=7 Hz).

DESCRIPTION 2(h)

4,5-Dihydro-10H-1-methyl-10-oxobenzo[5,6]-cyclohetpa[1,2-b]pyrrole-2-acetic acid-3-carboxylic acid

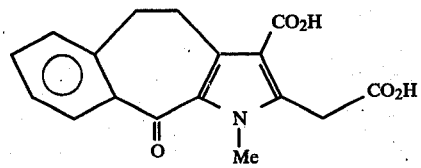

The crude diester (23.57 g, 0.064 mole) from Description 2(f) was hydrolyzed with 25% aqueous sodium hydroxide (310 ml) in the manner outlined in Description 1(g) to give the required diacid (16.65 g, 83%), δ((CD$_3$)$_2$CO/CD$_3$OD) 7.67–7.92 (1H, m), 7.57–7.07 (3H, m), 4.27 (2H, s), 3.94 (3H, s) and 3.47–2.87 (4H, m).

DESCRIPTION 2(i)

Ethyl 4,5-dihydro-10H-1-methyl-10-oxo-benzo[5,6]cyclohepta[1,2-b]pyrrole-2-acetate-3-carboxylic acid

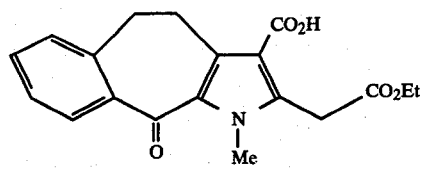

The crude diacid (15.65 g, 0.05 mole) from Description 2(h) was selectively esterified with 0.5% HCl/EtOH (200 ml) by the method given in Description 1(h) to give the required product (14.35 g, 84%) as a pale pink solid, δ(CDCl$_3$/C$_5$D$_5$N) 7.7–8.0 (1H, m), 7.0–7.5 (3H, m), 4.33 (2H, s), 4.15 (2H, q, J=7 Hz), 3.93 (3H, s), 3.7–2.8 (4H, m) and 1.21 (3H, q, J=7 Hz).

DESCRIPTION 2(j)

Ethyl 4,5-dihydro-10H-1-methyl-10-oxobenzo-[5,6]cyclohepta[1,2-b]pyrrole-2-acetate

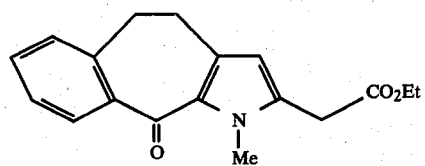

The acid (14 g, 0.041 mole) from Description 2(i) was decarboxylated under nitrogen at 180°-200° for 2 hours using the method given in Description 1(i). After purification by column chromatography on silica gel eluted with 1:1 ether:60°-80° petroleum ether the product was obtained as a pale yellow solid (5.83 g, 64% based on acid converted), m.p. 69°-70° after recrystallization from 60°-80° petrol, δ(CDCl$_3$) 8.0–7.7 (1H, m), 7.4–6.9 (3H, m), 5.9 (1H, s), 4.15 (2H, q, J=7 Hz), 3.89 (3H, s), 3.6 (2H, s), 3.2–2.7 (4H, m) and 1.25 (3H, t, J=7 Hz). (Found: C, 72.54; H, 6.42; N, 4.66. $C_{18}H_{19}NO_3$ requires: C, 72.71; H, 6.44; N, 4.71%).

EXAMPLE 2

4,5-Dihydro-10H-1-methyl-10-oxobenzo[5,6]-cyclohepta[1,2-b]pyrrole-2-acetic acid

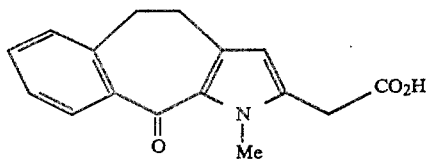

The ester (3.6 g, 0.012 mole) in 1 N sodium hydroxide (80 ml) and ethanol (70 ml) was heated at reflux for 1½ hours. After cooling the aqueous solution was extracted with ether (3×100 ml), filtered, and acidified with dilute hydrochloric acid to give an off-white solid which became pink on standing. The solid was collected, dried and recrystallized from chloroform/hexane to give the required product as a white crystalline solid (2.07 g, 64%), m.p. 164°–166°, δ(CDCl$_3$/C$_5$D$_5$N) 8.0–7.8 (1H, m), 7.4–7.0 (3H, m), 5.95 (1H, s), 3.93 (3H, s), 3.67 (2H, s) and 3.2–2.7 (4H, m).

EXAMPLE 3

4,5-Dihydro-10H-1-methyl-10-oxobenzo[5,6]cyclohepta[1,2-b]-2-pyrryl-2-propionic acid

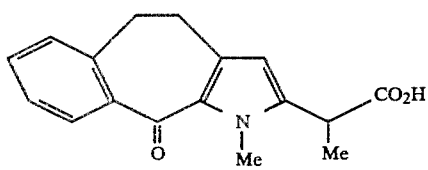

A solution of diisopropylamine (0.84 ml, 0.006 mole) in dry tetrahydrofuran (15 ml) was treated at −20° under nitrogen with a solution of n-butyllithium in hexane (2.7 ml, 1.95 M; 0.0052 mole) and then warmed to room temperature over 20 minutes.

A solution of 4,5-dihydro-10H-1-methyl-10-oxo benzo[5,6]cyclohepta[1,2-b]pyrrole-2-acetic acid (700 mg, 0.0026 mole) in dry tetrahydrofuran (20 ml) was added and the resulting deep red mixture was left stirring at room temperature for 2½ hours. Methyl iodide (0.16 ml, 0.0026 mole) was added and after a further 1½ hours at room temperature, water (5 ml) was added, followed by dilute hydrochloric acid (1 ml). The product was extracted into chloroform, dried (Na$_2$SO$_4$) and concentrated. The crude product was recrystallised from an ether/petrol mixture to afford the pure titled compound as a white solid, m.p. 96°–97°, δ(CDCl$_3$) 11.1 (1H, s), 8.0–7.8 (1H, m), 7.4–7.0 (3H, m), 5.95 (1H, s), 3.90 (3H, s), 4.0–3.5 (1H, m), 3.2–2.7 (4H, m) and 1.50 (3H, d, J=7 Hz).

DESCRIPTION 4(a)

5-Benzyl dimethyl 4-(2-phenyl)ethylpyrrole-2-(3'-propanoate)-3,5-dicarboxylate

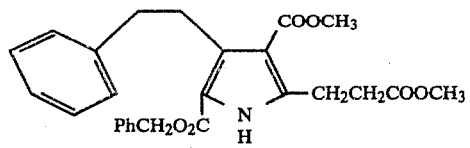

Sodium nitrite (26 g, 0.38 mole) in water (45 ml) was added dropwise with stirring to a solution of the crude benzyl ester from Description 2(b) (73.6 g, 0.26 mole, based on 90% purity) in glacial acetic acid (300 ml) between 5° and 7° C. After completing the addition, the mixture was stirred for a further 30 minutes at 0° C. and then for 2 hours at room temperature. The resulting solution was added slowly to a solution of dimethyl 3-oxo-adipate (67.7 g, 0.36 mole) in glacial acetic acid (250 ml) at 70° C. with concurrent addition of a mixture of zinc powder (82 g, 90%, 1.13 mole) and anhydrous sodium acetate (90 g, 1.13 mole) so that the temperature was kept at about 90° C. After these additions, the mixture was stirred at 100° C. for 1¼ hours before pouring into cold water (6 liters). With vigorous stirring a yellow solid crystallised out, which was filtered off, washed with water and then purified by recrystallisation from a 1:3 toluene:60°–80° petrol mixture to give the title pyrrole as a pale yellow solid (41.2 g, 32%), n.m.r. δ(CDCl$_3$) 9.85 (1H, br., s), (7.41 (5H, s), 7.3–7.1 (5H, m), 5.33 (2H, s), 3.86 (3H, s), 3.69 (3H, s) and 3.5–2.5 (8H, broad symmetrical multiplet).

DESCRIPTION 4(b)

5-Benzyl dimethyl 1-methyl-4-(2-phenyl)ethylpyrrole-2-(3'-propanoate)-3,5-dicarboxylate

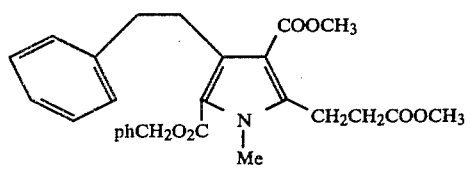

The above dimethyl ester (41.2 g, 0.092 mole) was refluxed for 24 hours in iso-butyl methylketone (400 ml) with anhydrous potassium carbonate (41.7 g, 0.30 mole) and dimethyl sulphate (32 ml, 0.34 mole), then cooled and poured into water (1 liter). The mixture was extracted with ether (3×200 ml) and the organic layers then combined and washed with water (2×200 ml), dried (anhydrous MgSO$_4$) and concentrated to leave a red oil. This was purified by column chromatography on silica gel (400 g) eluting with 1:1 60°–80° petrol:ether followed by recrystallisation from 3:1 toluene:60°–80° petrol to give a white solid (29.4 g, 69%), n.m.r. δ(CDCl$_3$) 7.30 (5H, s), 7.2–6.8 (5H, m), 5.22 (2H, s), 3.80 (3H, s), 3.77 (3H, s), 3.62 (3H, s) and 3.4–2.4 (8H, broad symmetrical multiplet).

DESCRIPTION 4(c)

Dimethyl 1-methyl-4-(2-phenyl)ethylpyrrole-2-(3'-propanoate-3-carboxylate-5-carboxylic acid

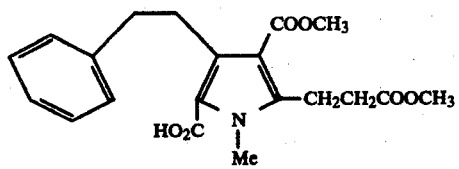

The above N-methylpyrrole triester (29.4 g, 0.063 mole) was hydrogenated at atmospheric pressure with 10% Pd/C (1.5 g) in ethyl acetate (400 ml). The catalyst was filtered off and the filtrate concentrated to give a white solid (22.5 g, 95%), m.p. 143°–145° C., n.m.r. δ(CDCl$_3$) 11.40 (1H, br., s), 7.13 (5H, s), 3.82 (3H, s), 3.75 (3H, s), 3.63 (3H, s), and 3.5–2.5 (8H, broad symmetrical multiplet).

DESCRIPTION 4(d)

Dimethyl 4,5-dihydro-10H-1-methyl-10-oxo-benzo[5,6]cyclohepta[1,2-b]pyrrole-2-(3'-propanoate)-3-carboxylate

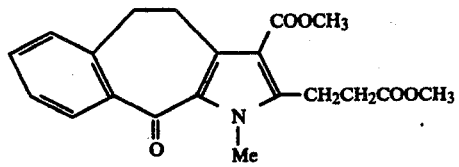

The above acid (22.5 g, 0.06 mole) was dissolved in dry toluene (350 ml), treated with oxalyl chloride (8 ml, 0.09 mole) and stirred at room temperature for 1 hour, followed by 2 hours under reflux. The solvent was evaporated off to leave a red oil. This red oil was dissolved in dichloromethane (300 ml), powdered aluminium chloride (16.1 g, 0.12 mole) added and reaction mixture stirred at room temperature for 4 hours. The solution was then carefully poured with stirring into ice/water, the organic layer was separated and the aqueous layer was further extracted with chloroform (2×300 ml). The organic extracts were then combined, washed with saturated aqueous sodium bicarbonate (2×200 ml), then with water (2×200 ml), dried (anhydrous MgSO$_4$) and concentrated to give a brown oil. This crude product was purified by column chromatography on silica gel (500 g) eluting with 60°–80° petrol rising to 1:1 petrol:ether to give the titled compound (72%), n.m.r. δ(CDCl$_3$) 7.8–7.6 (1H, m), 7.3–7.0 (3H, m), 3.83 (3H, s), 3.68 (3H, s), 3.55 (3H, s), and 3.4–2.4 (8H, m); u.v. (EtOH)λ$_{max}$ 318 nm.

DESCRIPTION 4(e)

4,5-Dihydro-10H-1-methyl-10-oxo-benzo[5,6]cyclohepta[1,2-b]pyrrole-2-propanoic acid-3-carboxylic acid

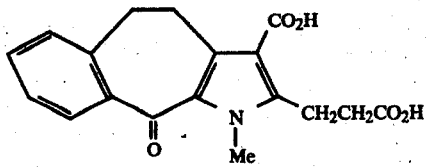

A sample of the above tricyclic diester (3.20 g, 0.0090 mole) was refluxed in 25% aqueous NaOH (50 ml) and ethanol (10 ml) for 2 hours. The solution was then cooled and poured into water (100 ml) before washing with ether (2×40 ml), and acidifying the aqueous layer with dilute hydrochloric acid. The resulting solution was extracted with chloroform (2×50 ml), the organic layer separated, washed with water (2×20 ml), dried (anhydrous MgSO$_4$) and evaporated to dryness to give the title diacid as a white solid (2.80 g, 95%), n.m.r. δ(d$_6$-DMSO) 11.57 (2H, s), 7.7–7.5 (1H, m), 7.3–7.0 (3H, m), 3.85 (3H, s), 3.07 (4H, s) and 3.6–2.4 (4H, m).

DESCRIPTION 4(f)

4,5-Dihydro-10H-1methyl-10-oxo-benzo-[5,6]cyclohepta[1,2-b]pyrrole-2-propanoic acid

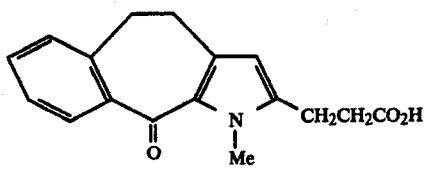

The above diacid (2.80 g, 0.0086 mole) was heated under nitrogen at 190°–200° C. in an oil bath for 3½ hours. The crude product was purified by dissolving in ethyl acetate (100 ml), extracting with saturated aqueous sodium bicarbonate solution (2×100 ml), combining the aqueous layers and acidifying with dilute hydrochloric acid. The acidic solution was extracted with ethyl acetate (2×80 ml), the organic layers combined, washed with water (2×50 ml), dried (anhydrous MgSO$_4$) and evaporated to dryness to give 4,5-dihydro-10H-1-methyl-10-oxo-benzo[5,6]cyclohepta[1,2-b]pyrrole-2-propionic acid. n.m.r. δ(CDCl$_3$) 9.93 (1H, br., s), 7.9–7.7 (1H, m), 7.3–7.0 (3H, m), 5.78 (1H, s), 3.87 (3H, s) and 3.3–2.5 (8H, m).

EXAMPLE 4

4-(4,5-Dihydro-10H-1-methyl-10-oxo-benzo[5,6]cyclohepta[1,2-b]-2-pyrryl)butan-2-one

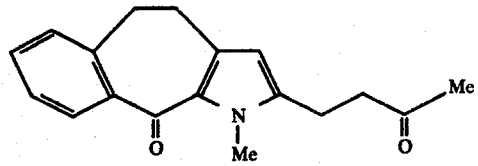

A sample of the above propionic acid (1.41 g, 0.0051 mole) was dissolved in dry tetrahydrofuran (30 ml) together with dry triethylamine (0.69 ml, 0.0051 mole)

at −25° C. Ethylchloroformate (0.48 ml, 0.0051 mole) was added dropwise and the solution stirred at −20° C. for 1 hour before stirring at the same temperature for 24 hours prior to use. The white precipitate was filtered off and the filtrate added at 0° C. to a solution prepared by the treatment of bis(trimethylsilyl)malonate (2.48 g, 0.011 mole) in dry ether (50 ml) under nitrogen at −65° C. with a solution of n-butyllithium in hexane (8.7 ml, 1.15 M; 0.011 mole). The resulting solution was stirred at 0° C. for 20 minutes before quenching the reaction by addition of 5% aqueous sodium bicarbonate (100 ml). The aqueous layer was separated and the organic layer further extracted with sodium bicarbonate solution (2×50 ml) before combining the aqueous layers and acidifying with dilute hydrochloric acid. The acidic solution was extracted with ethyl acetate (2×100 ml), the organic layers then combined and washed with water (2×100 ml) and evaporated to dryness to give a brown oil. This was heated at 70°–80° C. in dimethyl sulphoxide (20 ml) for 30 minutes until gas evolution ceased. The solution was poured into saturated aqueous sodium bicarbonate (100 ml) and the resulting solution extracted with ethyl acetate (2×80 ml). The organic layers were combined, washed with water (2×50 ml), dried (anhydrous MgSO₄) and concentrated to give a light brown solid. This was purified by recrystallisation from 1:1 60°–80° petrol:ether to give the titled compound as a white, crystalline solid, m.p. 114°–115° C., n.m.r. δ(CDCl₃) 8.0–7.8 (1H, m), 7.3–7.0 (3H, m). 5.72 (1H, s), 3.88 (3H, s), 3.0–2.8 (4H, m), 2.78 (4H, s), and 2.17 (3H, s).

DESCRIPTION 4(g)

4-(4,5-Dihydro-10H-1-methyl-10-oxobenzo[5,6]cyclohepta[1,2-b]-2-pyrryl)but-1-ene

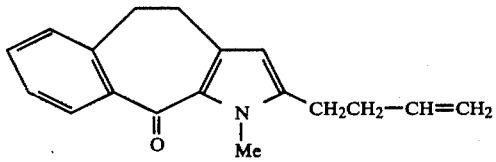

A solution of 4,5-dihydro-10H-1-methyl-10-oxo-benzo[5,6]cyclohepta[1,2-b]pyrrole-2-acetic acid (560 mg, 0.0021 mole) in dry tetrahydrofuran (20 ml) was added slowly at 0° to a solution of diisopropylamine (0.7 ml, 0.005 mole) in dry tetrahydrofuran (20 ml) previously treated at −65° with n-butyllithium in hexane (3.7 ml, 0.0042 mole). The resulting deep red solution was allowed to come to room temperature over 2 hours and then heated at 55° for a ½ hour.

On cooling at 0°, allyl bromide (0.18 ml, 0.0021 mole) was added and the mixture was stirred at room temperature for 1 hour and then at 55° for 2 hours. On cooling to 0° the mixture was treated with water (10 ml) before being partitioned between ether (50 ml) and dilute, aqueous sodium bicarbonate solution (20 ml, 1 N). The aqueous layer was acidified with dilute hydrochloric acid before being extracted with ether (3×25 ml). The combined ethereal extracts were washed with water (2×10 ml), dried (MgSO₄) and concentrated to leave a red oil (500 mg).

The above oil (500 mg) was heated under nitrogen for 1 hour at about 150°, cooled and taken up into ether (50 ml). The organic extract was washed with dilute aqueous sodium bicarbonate solution (2×20 ml, 1 N), water (20 ml) before being dried (Na₂SO₄) and concentrated to leave a dark red solid. This crude material was chromatographed on a silica column (20 g) using 10% ethereal petrol as eluant. Recrystallisation of the solid from 60°–80° petrol gave pure 4-(4,5-dihydro-10H-1-methyl-10-oxobenzo[5,6]cyclohepta[1,2-b]-2-pyrryl)but-1-ene (250 mg); m.p. 100°–101°.

EXAMPLE 4

Alternative Preparation

The butene (0.43 g, 0.0016 mole) from Description 4(g) was added to a suspension of copper(I) chloride (0.16 g) and palladium (II) chloride (0.06 g) in water (0.25 ml)/DMF (2 ml) which had been previously oxygenated for 1½ hours by shaking while passing air through the mixture. The shaking and aeration was continued for a further 1½ hours and then the reaction mixture poured into water (50 ml) and extracted with chloroform (3×20 ml). The combined organic extracts were washed with water (4×20 ml), dried (MgSO₄) and evaporated to dryness. The residue was chromatographed on silica gel with 1:1 ether:60°–80° petroleum ether as eluant to give 4-(4,5-dihydro-10H-1-methyl-10-oxobenzo[5,6]cyclohepta[1,2-b]-2-pyrryl)butan-2-one having physical data identical to that disclosed above.

EXAMPLE 5

4-(4,5-Dihydro-10H-1-methyl-10-oxo-benzo[5,6]cyclohepta[1,2-b]-2-pyrryl)butan-2-ol

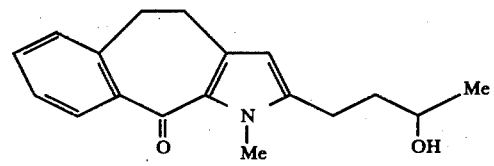

A mixture of the above butanone (330 mg, 0.0011 mole) and sodium borohydride (53 mg, 0.0014 mole) was stirred for 40 minutes at room temperature. After the addition of saturated aqueous ammonium chloride solution (10 ml) the mixture was concentrated and the residue partitioned between chloroform (20 ml) and water (20 ml). The chloroform layer was washed with water (10 ml), dried (Na₂SO₄) and concentrated. The crude product was purified by column chromatography using ether as eluant to give the title compound (300 mg), δ(CDCl₃) 8.05–7.8 (1H, m), 7.4–7.0 (3H, m), 5.82 (1H, s), 3.90 (3H, s), 4.1–3.6 (1H, m), 3.1–2.5 (7H, m), 1.9–1.5 (2H, m) and 2.21 (2H, d, J=6 Hz).

EXAMPLE 6

2-Acetoxy-4-(4,5-dihydro-10H-1-methyl-10-oxo-benzo[5,6]cyclohept[1,2-b]-2-pyrryl)butane

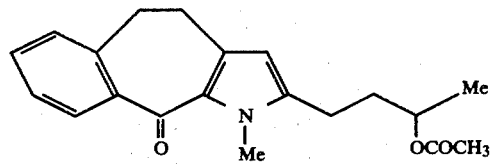

A mixture of the above butanol (283 g, 0.001 mole) dry toluene (30 ml) and dry pyridine (0.4 ml) was cooled with an ice bath and treated dropwise with acetyl chloride (0.2 ml, 0.0028 mole). After stirring at room temperature for an hour, the solution was treated with cold water (30 ml) before being extracted with ether (2×20 ml). The organic layer was washed with water, 1H HCl, water again, dried (Na2SO4) and concentrated. The crude product was chromatographed on a neutral alumina column using ether as eluant to afford the titled compound (260 mg), δ(CDCl3) 8.05–7.8 (1H, m), 7.4–7.0 (3H, m), 5.80 (1H, s), 5.15–4.75 (1H, m), 3.90 (3H, s), 3.1–2.4 (6H, m), 2.2–1.6 (2H, m), 2.01 (3H, s) and 1.24 (3H, d, J=6 Hz).

DESCRIPTION 7(a)

Ethyl 3-oxo-5-[3-chlorophenyl]pentanoate

Ethyl acetoacetate (78.6 g, 0.6 mole) was added to a slurry of sodium hydride (20.8 g of 75% dispersion in oil, 0.65 mole) in dry THF at 0° C. under nitrogen followed by addition of n-butyl lithium (390 ml, 1.6 M in hexane, 0.63 mole) by the method given in Description 1(a). 3-Chlorobenzyl chloride (100 g, 0.62 mole) was added and after work-up and purification by vacuum distillation the required product was obtained as a very pale yellowish green oil (97.3 g, 64%), δ(CDCl3) 7.3–6.9 (4H, m), 4.18 (2H, q, J=7 Hz), 3.42 (2H, s), 2.88 (4H, s), and 1.27 (3H, t, J=7 Hz).

DESCRIPTION 7(b)

Benzyl 3-oxo-5-[3-chlorophenyl]pentanoate

The ethyl ester (95.61 g, 0.3 mole assuming 80% purity) was heated for 5 hours between 190°–225° C. under nitrogen with benzyl alcohol (32.5 g, 0.3 mole) to give the required product, δ(CDCl3) 7.31 (5H, s), 7.4–6.8 (4H, m), 5.12 (2H, s), 3.44 (2H, s), and 2.83 (4H, s).

DESCRIPTION 7(c)

5-Benzyl diethyl 4-[2-(3'-chlorophenyl)ethyl]-pyrrole-2-acetate-3,5-dicarboxylate

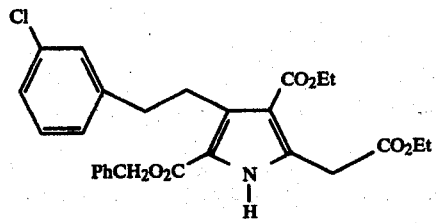

The crude benzyl ester (25 g, 0.0592 mole when assumed to be 75% pure) was converted to the title compound by the method of Knorr pyrrole synthesis given in Description 1(c) using zinc (16.6 g), sodium acetate (18.7 g) and diethyl acetone-1,3-dicarboxylate (15.47 g). The crude product was crystallized from toluene/6-0°–80° petroleum ether and washed with a little cold ethanol to afford the required product (13.33 g, 45%) as a granular white solid, m.p. 117°–122°, δ(CDCl3) 10.25 (1H, br., s), 7.36 (5H, s), 7.25–6.75 (4H, m), 5.27 (2H, s), 4.29 (2H, q, J=7 Hz), 4.18 (2H, q, J=7 Hz), 4.04 (2H, s), 3.55–2.35 (4H, symmetrical m), 1.33 (3H, t, J=7 Hz) and 1.25 (3H, t, J=7 Hz).

DESCRIPTION 7(d)

5-Benzyl diethyl 4-[2-(3'-chlorophenyl)ethyl]-1-methylpyrrole-2-acetate-3,5-dicarboxylate

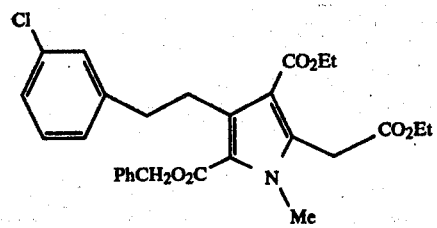

The N-H pyrrole (49.61 g, 0.0996 mole) from Description 7(c) was methylated with dimethyl sulphate (20 ml) and potassium carbonate (50 g) in isobutyl methyl ketone (450 ml) by the method given in Description 2(d). The product was obtained as a white crystalline solid (34.98 g, 69%), δ(CDCl3) 7.29 (5H, s), 7.25–6.6 (4H, m), 5.23 (2H, s), 4.25 (2H, q, J=7 Hz), 4.18 (2H, q, J=7 Hz), 4.09 (2H, s), 3.8 (3H, s), 3.55–2.3 (4H, symmetrical m), 1.31 (3H, t, J=7 Hz), and 1.24 (3H, t, J=7 Hz).

DESCRIPTION 7(e)

Diethyl 4-[2-(3'-chlorophenyl)ethyl]-1-methylpyrrole-2-acetate-3-carboxylate-5-carboxylic acid

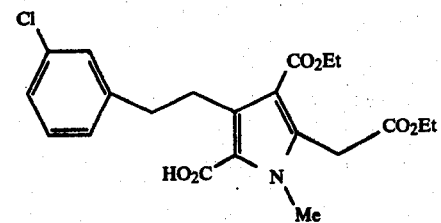

The benzyl ester (34 g, 0.07 mole) from Description 7(d) was hydrogenated at atmospheric pressure for 1¼ hours by the method given in Description 2(e) to give the required acid (22.29 g, 77%) after washing the resulting ethyl acetate filtrate with dilute sodium hydroxide and then acidifying the aqueous with dilute hydrochloric acid, δ(CDCl3/(CD3)2SO) 7.3–7.0 (4H, m), 6.91 (1H, br., s), 4.25 (2H, q, J=7 Hz), 4.15 (2H, q, J=7 Hz), 4.11 (2H, s), 3.81 (3H, s), 3.6–2.4 (4H, symmetrical m), 4.34 (3H, t, J=7 Hz) and 1.26 (3H, t, J=7 Hz).

DESCRIPTION 7(f)

Diethyl 7-chloro-4,5-dihydro-10H-1-methyl-10-oxobenzo[5,6-]cyclohepta[1,2-b]pyrrole-2-acetate-3-carboxylate The acid (17.2 g, 0.041 mole) from Description 7(e) was converted to its acid chloride with oxalyl chloride (7.77 g, 1.5 equiv.) and cyclized to the title compound using aluminium trichloride (17.4 g, 0.13 mole) in tetrachloroethane (500 ml) at 120° C. for 20 mins. After work-up by the method given in Description 2(f) the crude product was purified by column chromatography on silica gel (200 g) with ether as eluant followed by recrystallization from toluene/60°-80° petroleum to give a pale yellow solid (4.89 g, 28%), δ(CDCl$_3$) 7.8 (1H, d, J=9 Hz), 7.3-7.01(2H, m), 4.25 (2H, q, J=7 Hz), 4.15 (2H, q, J=7 Hz), 4.1 (2H, s), 3.9 (3H, s), 3.5-2.8(4H, m), 1.32 (3H, t, J=7 Hz) and 1.25 (3H, t, J=7 Hz).

DESCRIPTION 7(g)

7-Chloro-4,5-dihydro-10H-1-methyl-10-oxobenzo-[5,6]cyclohepta[1,2-b]pyrrole-2-acetic acid-3-carboxylic acid

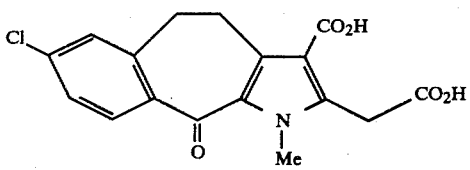

The diester (4.26 g, 0.0106 mole) from Description 7(f) was hydrolysed with 25% sodium hydroxide (55 ml) by the method outlined in Description 1(g) to give the required diacid (3.49 g, 95%), δ((CD$_3$)$_2$SO) 12.25 (2H, br.,s), 7.68 (1H, d, J=9 Hz), 7.54-7.11 (2H, m), 4.18 (2H, s), 3.84 (3H, s) and 3.55-2.57 (4H, m).

DESCRIPTION 7(h)

Ethyl 7-chloro-4,5-dihydro-10H-1-methyl-10-oxobenzo[5,6-]cyclohepta[1,2-b]pyrrole-2-acetate-3-carboxylic acid

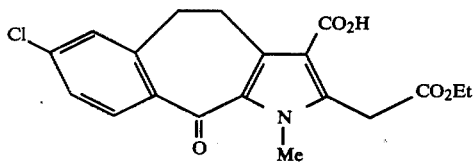

The diacid (3.43 g, 0.00987 mole) from Description 7(g) was selectively esterified with 0.5% HCl/EtOH (60 ml) by the method given in Description 1(h) to give the title compound as a white crystalline solid (3.28 g, 88%), δ(CDCl$_3$) 10.75 (1H, br., s), 7.75 (1H, d, J=9 Hz), 7.35-7.0 (2H, m), 4.19 (2H, s), 4.17 (2H, q, J=7 Hz), 4.92 (3H, s), 3.6-2.8 (4H, m) and 1.26 (3H, t, J=7 Hz).

DESCRIPTION 7(i)

Ethyl 7-chloro-4,5-dihydro-10H-1-methyl-10-oxobenzo[5,6-]cyclohepta[1,2-b]pyrrole-2-acetate

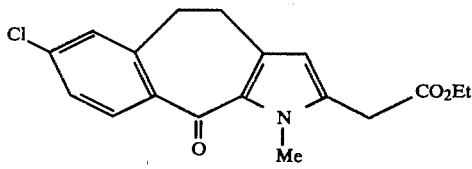

The acid (3.22 g, 0.0086 mole) from Description 7(h) was decarboxylated by heating to 200°-230° for 2½ hours under nitrogen after the method given in Description 1(i). Purification by column chromatography on silica gel eluted with 1:1 ether:60°-80° petroleum ether gave the required product as a yellow solid (2.09 g, 74%), δ(CDCl$_3$) 7.83 (1H, d, J≈8 Hz), 7.35-7.05 (2H, m), 5.92 (1H, s), 4.16 (2H, q, J=7 Hz), 3.9 (3H, s), 3.62 (2H, s), 3.2-2.65 (4H, m) and 1.23 (3H, t, J=7 Hz).

EXAMPLE 7

7-Chloro-4,5-dihydro-10H-1-methyl-10-oxobenzo[5,6-]cyclohepta[1,2-b]pyrrole-2-acetic acid

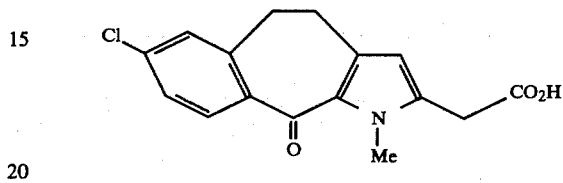

The ester (0.98 g, 0.00296 mole) from Description 7(i) was hydrolysed to the required acid by the method given in Example 1. After recrystallization from a mixture of chloroform/methanol/60°-80° petrol the acid was obtained as pale yellow needles (0.72 g, 80%), m.p. 182°-185° (dec), M+ =303.0687, δ(CDCl$_3$/(CD$_3$)$_2$SO) 8.94 (1H, br., s), 7.82 (1H, d, J≈9 Hz), 7.4-7.0 (2H, m), 5.91 (1H, s), 3.88 (3H, s), 3.59 (2H, s), and 3.2-2.65 (4H, m); λ$_{max}$ (EtOH) 259 (ε=7.78×10$^3$) and 336 nm (ε=1.82×10$^4$).

DESCRIPTION 8(a)

Ethyl 5-(3-fluorophenyl)-3-oxopentanoate

3-Fluorobenzyl chloride (75 g, 0.519 mole) was reacted with the dianion formed by addition of ethyl acetoacetate (67.75 g, 0.52 mole) to a slurry of sodium hydride (17.93 g) in dry THF (1.2 L) followed by addition of butyl lithium (336 ml, 1.6 M) by the method given in Description 1(a). The product was obtained as a colourless oil after vacuum distillation, b.p. 142°-150°, 0.4 mmHg, δ(CCl$_4$) 7.3-6.5 (4H, m), 4.01 (2H, q, J=7 Hz), 3.22 (2H, s), 2.72 (4H, s), 1.1 (3H, t, J=7 Hz).

DESCRIPTION 8(b)

Benzyl 5-(3-fluorophenyl)-3-oxopentanoate

The ethyl ester (80.3 g, 0.337 mole) from Description 8(a) was treated under nitrogen with benzyl alcohol (49 ml) by the method in Description 1(b) to give the title compound (91.26 g), δ(CCl$_4$) 7.14 (5H, s), 7.13-6.47 (4H, m), 4.95 (2H, s), 3.21 (2H, s) and 2.9-2.5 (4H, m).

DESCRIPTION 8(c)

5-Benzyl diethyl 4[2-(3'-fluorophenyl)ethyl]pyrrole-2-acetate-3,5-dicarboxylate

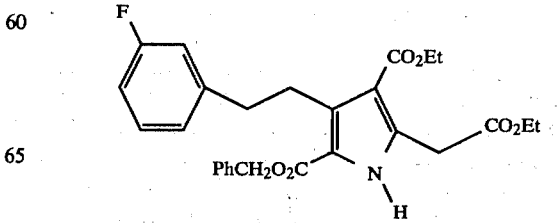

The benzyl ester (91.29 g, 90% pure, 0.274 mole) from Description 8(b) was reacted in a Knorr pyrrole synthesis by the method given in Description 1(c) with sodium nitrite (25 g), zinc (77.3 g) and diethylacetone-1,3-dicarboxylate (65 ml) to give the title compound as a white crystalline solid (68.5 g, 52%), m.p. 119°–121° after recrystallization from toluene/60°–80° petroleum ether, δ(CDCl$_3$) 10.13 (1H, br., s), 7.32 (5H, s), 7.25–6.55 (4H, m), 5.27 (2H, s), 4.28 (2H, q, J=7 Hz), 4.18 (2H, q, J=7 Hz), 4.03 (2H, s), 3.55–2.45 (4H, symmetrical m), 1.33 (3H, t, J=7 Hz) and 1.25 (3H, t, J=7 Hz). (Found: C, 67.24; H, 5.88; N, 2.90; F, 3.92. C$_{27}$H$_{28}$FNO$_6$ requires: C, 67.35; H, 5.86; N, 2.91; F, 3.95%)

DESCRIPTION 8(d)

5-Benzyl diethyl 4-[2-(3'-fluorophenyl)ethyl]-1-methylpyrrole-2-acetate-3,5-dicarboxylate

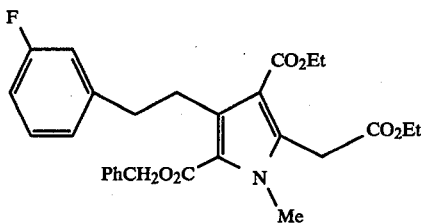

The N-H pyrrole (68.5 g, 0.142 mole) from Description 8(c) was methylated with dimethyl sulphate (45 ml) by the general method given in Description 2(d) to give the desired N-methylpyrrole as a white solid (52.19 g, 74%), m.p. 81°–85°, δ(CDCl$_3$) 7.32 (5H, s), 7.3–6.4 (4H, m), 5.24 (2H, s), 4.3 (2H, q, J=7 Hz), 4.19 (2H, q, J=7 Hz), 4.08 (2H, s), 3.81 (3H, s), 3.55–2.45 (4H, symmetrical m), 1.28 (3H, t, J=7 Hz), and 1.22 (3H, t, J=7 Hz). (Found: C, 68.22; H, 6.23; N, 2.84. C$_{28}$H$_{30}$FNO$_6$ requires: C, 67.86; H, 6.10; N, 2.83%).

DESCRIPTION 8(e)

Diethyl 4-[2-(3'-fluorophenyl)ethyl]-1-methyl-pyrrole-2-acetate-3-carboxylate-5-carboxylic acid

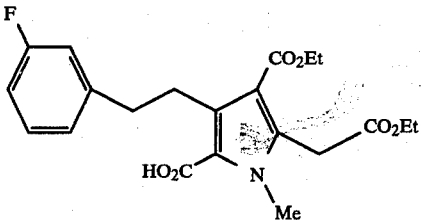

The benzyl ester (52.19 g, 0.105 mole) from Description 8(d) was hydrogenated at atmospheric pressure by the method given in Description 2(e) to give the required acid as a white solid (41.0 g, 96%), m.p. 151°–154°, δ(CDCl$_3$) 7.45–6.5 (4H, m), 4.29 (2H, q, J=7 Hz), 4.18 (2H, q, J=7 Hz), 4.12 (2H, s), 3.85 (3H, s), 3.7–2.5 (4H, symmetrical m), 1.33 (3H, t, J=7 Hz) and 1.26 (3H, t, J=7 Hz). (Found: C, 62.33; H, 5.84; N, 3.46. C$_{21}$H$_{24}$FNO$_6$ requires: C C, 62.21; H, 5.97; N, 3.46%).

DESCRIPTION 8(f)

Diethyl 4,5-dihydro-7-fluoro-10H-1-methyl-10-oxobenzo[5,6-]cyclohepta[1,2-b]pyrrole-2-acetate-3-carboxylate

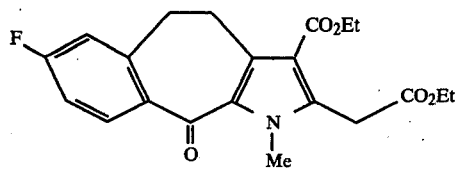

The acid (39.74 g, 0.098 mole) from Description 8(e) was converted to its acid chloride with oxalyl chloride (26.2 g) and cyclised to the title compound using aluminium trichloride (19.5 g) in dichloromethane (700 ml) by the method given in Description 2(f). The crude product was recrystallized from ethyl acetate/60°–80° petroleum ether as pale yellow needles (21.9 g, 58%), δ(CDCl$_3$) 7.83 (1H, dd, J≈9 and 6 Hz), 7.15–6.6 (2H, m), 4.28 (2H, q, J=7 Hz), 4.18 (2H, q, J=7 Hz), 4.15 (2H, s), 3.93 (3H, s), 3.5–2.6 (4H, m), 1.35 (3H, t, J=7 Hz) and 1.27 (3H, t, J=7 Hz).

DESCRIPTION 8(g)

4,5-dihydro-7-fluoro-10H-1-methyl-10-oxobenzo[5,6-]cyclohepta[1,2-b]pyrrole-2-acetic acid-3-carboxylic acid

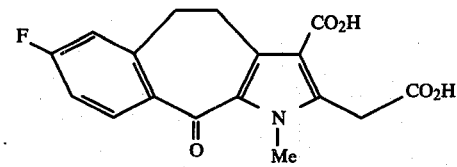

The diester (18.51 g, 0.048 mole) from Description 8(f) was hydrolyzed with 25% sodium hydroxide solution (250 ml) and ethanol (20 ml). Work-up by the method given in Description 1(g) gave the required diacid (15.81 g, quantitative yield) as a white solid, δ((CD$_3$)$_2$SO) 12.44 (2H, br., s) 7.77 (1H, dd, J≈6 and 9 Hz), 7.4–6.5 (2H, m), 4.15 (2H, s), 3.82 (3H, s), and 3.5–2.7 (4H, m).

DESCRIPTION 8(h)

Ethyl 4,5-dihydro-7-fluoro-10H-1-methyl-10-oxobenzo[5,6-]cyclohepta[1,2-b]pyrrole-2-acetate-3-carboxylic acid

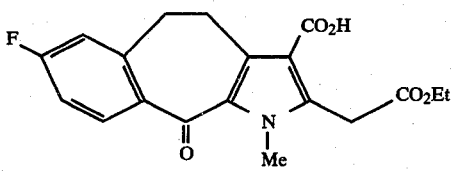

The diacid (15.64 g, 0.047 mole) from Description 8(g) was selectively esterified with 0.5% HCl/EtOH by the method given in Description 1(h) to give the required monoester (15.15 g, 89%), δ(CDCl$_3$/(CD$_3$)$_2$SO/C$_5$D$_5$N) 9.55 (1H, br., s), 7.89 (1H, dd, J≈9 and 6 Hz), 7.2–6.6 (2H, m), 4.23 (2H, s), 4.15

(2H, q, J=7 Hz), 3.9 (3H, s), 3.6–2.7 (4H, m), and 1.23 (3H, t, J=7 Hz).

DESCRIPTION 8(i)

Ethyl 4,5-dihydro-7-fluoro-10-H-1-methyl-10-oxobenzo[5,6-]cyclohepta[1,2-b]pyrrole-2-acetate

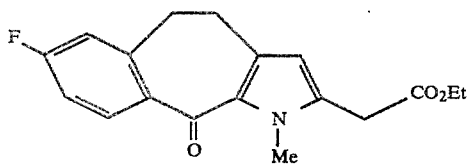

The mono acid (15.1 g, 0.042 mole) from Description 8(h) was decarboxylated by the method given in Description 1(i). The crude product was purified by column chromatography on silica gel (350 g) with 1:1 ether: 60°–80° petroleum ether as eluant and was obtained as a pale yellow solid (6.67 g, 64% taking into account recovered starting material), m.p. 80°–83°, δ(CDCl₃) 7.92 (1H, dd, J≈6 and 9 Hz), 7.2–6.6 (2H, m), 5.92 (1H, s), 4.16 (2H, q, J=7 Hz), 3.9 (3H, s), 3.62 (2H, s), 3.3–2.65 (4H, m) and 1.27 (3H, t, J=7 Hz).

EXAMPLE 8

4,5-Dihydro-7-fluoro-10H-1-methyl-10-oxobenzo[5,6-]cyclohepta[1,2-b]pyrrole-2-acetic acid

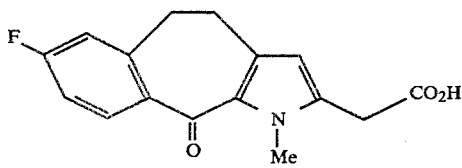

The ester (3 g, 0.0095 mole) was hydrolyzed with 1 N sodium hydroxide (80 ml) to give the required acid as a white solid (2.45 g, 90%), m.p. 168°–170°, δ(CDCl₃) 7.98 (1H, dd, J≈6 and 9 Hz), 7.3–6.3 (3H, overlapping m and br., s), 6.0 (1H, s), 3.93 (3H, s), 3.7 (2H, s), and 3.15–2.65 (4H, m), after working up by the methanol given in Example 1.

PHARMACOLOGICAL DATA SECTION

The compounds were examined for Anti-Inflammatory Activity in two conventional tests, the Cotton Pellet Granuloma test and the Carrageenin test.

The compounds were also examined for Analgesic Activity in the conventional phenyl quinone writhing test.

The results obtained are shown in the table.

No toxic effects were observed in any of these tests.

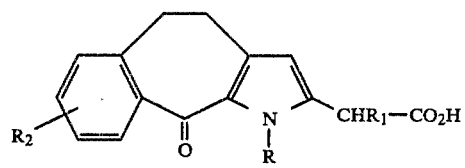

| $R_2$ | A | Cotton Pellet | Carrageenin | Writhing Analgesic Test |
|---|---|---|---|---|
| CH₃ | CH₂COOH | 25(34)* | 25(44)* | ED₅₀ 5.1 |
| Gastric Irritancy GTD₅₀ = 95 mg/kg | | | 5(21)* | |
| Cl | CH₂COOH | 25(49)* | 25(25)* | |

-continued

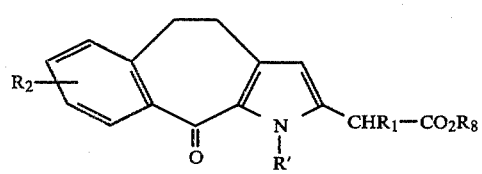

| $R_2$ | A | Cotton Pellet | Carrageenin | Writhing Analgesic Test |
|---|---|---|---|---|
| F | CH₂COOH | 10(31)* | | |
| H | CH₂COOH | 10(28)* | 45(30)* | ED₅₀ 2.4 |
| | | | 15(25)* | |
| H | CH₂CH₂COCH₃ | | 45(20)* | |
| | | | 15(17)* | |
| H | OCOCH₃ CH₂CH₂CHCH₃ | | 45(19)* 15(17)* | |
| H | CH₂CH₂CH(OH)CH₃ | | 45(25)* | |

What we claim is:

1. A compound selected from the group consisting of a carboxylic acid of the formula:

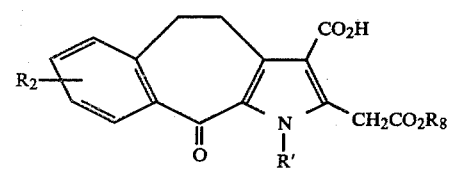

wherein
R is alkyl of 1 to 4 carbon atoms;
R₁ is hydrogen or alkyl of 1 to 4 carbon atoms and
R₂ is hydrogen, halo, alkyl of 1 to 4 carbon atoms, alkoxy of 1 to 4 carbon atoms or alkylthio of 1 to 4 carbon atoms; non-toxic in vivo hydrolysable esters and amides thereof and compounds of the said formula having its carboxylic acid group replaced by CHO or CH₂OH; and the pharmaceutically acceptable salts both of said carboxylic acids and the compounds having said replacements.

2. A compound according to claim 1 wherein R₂ is in the 7-position.

3. A compound according to claim 1 wherein R₂ is hydrogen.

4. A compound according to claim 1 wherein R₁ is hydrogen.

5. A compound of formula or

-continued

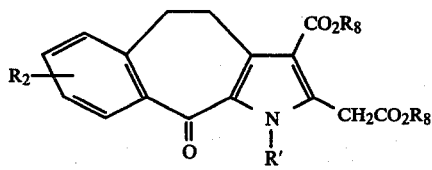

wherein R, $R_1$ and $R_2$ are as defined in claim 1, R' is hydrogen or $C_{1-4}$ alkyl, and $R_8$ is $C_{1-4}$ alkyl.

6. A compound selected from the group consisting of (i) carboxylic acids of the formula of claim 1:

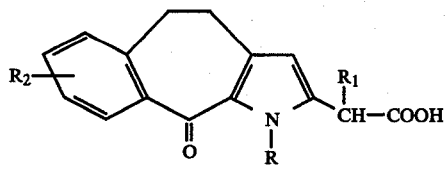

wherein
R is alkyl of 1 to 4 carbon atoms,
$R_1$ is hydrogen or alkyl of 1 to 4 carbon atoms, and
$R_2$ is hydrogen, ahlo, alkyl of 1 to 4 carbon atoms, alkoxy of 1 to 4 carbon atoms or alkylthio of 1 to 4 carbon atoms, (ii) the pharmaceutically acceptable alkali metal, alkaline earth metal and ammonium salts of said acids and (iii) the non-toxic in vivo hydrolysable esters of said acids.

7. A compound having the formula:

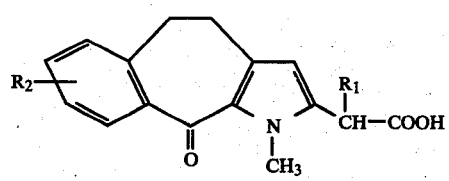

wherein
$R_1$ is hydrogen or methyl
$R^2$ is hydrogen, fluoro, chloro, bromo, methyl, ethyl, propyl, methoxy or methylthio, or a pharmaceutically acceptable alkali metal, alkaline earth metal or ammonium salt thereof.

8. The compound according to claim 6 which is 4,5-dihydro-1,7-dimethyl-10H-10-oxobenzo[5,6]cyclohepta[1,2-b]pyrrole 2-acetic acid.

9. The compound according to claim 6 which is 4,5-dihydro-1-methyl-10H-10-oxobenzo[5,6]cyclohepta[1,2-b]pyrrole-2-acetic acid.

10. The compound according to claim 6 which is 2-(4,5-dihydro-1-methyl-10H-10-oxobenzo[5,6]cyclohepta[1,2-b]pyrr-2-yl)propionic acid.

11. The compound according to claim 6 which is 4,5-dihydro-1-methyl-7-chloro-10H-10-oxobenzo[5,6-]cyclohepta[1,2-b]pyrrole-2-acetic acid.

12. The compound according to claim 6 which is 4,5-dihydro-1-methyl-7-fluoro-10H-10-oxobenzo[5,6-]cyclohepta[1,2-b]pyrrole-2-acetic acid.

* * * * *